United States Patent [19]

Ullman

[11] 4,160,016

[45] * Jul. 3, 1979

[54] RECEPTOR FLUORESCENT IMMUNOASSAY

[75] Inventor: Edwin F. Ullman, Atherton, Calif.

[73] Assignee: Syva Company, Palo Alto, Calif.

[*] Notice: The portion of the term of this patent subsequent to Dec. 21, 1993, has been disclaimed.

[21] Appl. No.: 823,765

[22] Filed: Aug. 11, 1977

Related U.S. Application Data

[63] Continuation-in-part of Ser. No. 796,916, May 16, 1977, abandoned, which is a continuation-in-part of Ser. No. 751,838, Dec. 17, 1976, abandoned, which is a continuation-in-part of Ser. No. 402,693, Oct. 2, 1973, Pat. No. 3,998,943.

[51] Int. Cl.² ............ G01N 21/38; G01N 31/00; G01N 33/16
[52] U.S. Cl. .................... 424/8; 23/230 B; 250/302; 424/11; 424/12; 424/13
[58] Field of Search ........... 424/1, 8, 11, 12, 13; 23/230 B; 195/103.5 A; 250/302

[56] References Cited

U.S. PATENT DOCUMENTS

| | | | |
|---|---|---|---|
| 3,641,235 | 2/1972 | Weiss | 424/8 |
| 3,720,760 | 3/1973 | Bennich | 424/8 X |
| 3,901,654 | 8/1975 | Gross | 23/230 B |
| 3,996,345 | 12/1976 | Ullman | 424/8 |
| 3,998,943 | 12/1976 | Ullman | 424/12 |

OTHER PUBLICATIONS

Williams, Methods in Immunol. & Immunochem., vol. III, 1971, Acad. Press, N.Y., pp. 395-406.
Dandliker, Immunochem., vol. 7, 1970, pp. 799-828.
Brand, Ann. Rev. Biochem., vol. 41, 1972, pp. 843-868.
Stryer, Science, vol. 162, p. 526 (1968).
Smith, FEBS Letters, vol. 77, p. 25 (1977).
Ullman, J. Biol. Chem., vol. 251, p. 4172 (1976).

*Primary Examiner*—Anna P. Fagelson
*Attorney, Agent, or Firm*—Bertram I. Rowland

[57] ABSTRACT

A novel sensitive method for determining qualitatively and quantitatively the presence of a wide variety of physiologically active organic compounds (ligand) and their receptors is provided. The method employs a reagent whch involves bonding a compound having structural similarity to the compound to be determined (ligand analog) to a fluorescing compound. The unknown compound is referred to as a ligand, the conjugate of the structurally similar compound and fluorescer is referred to as ligand analog-fluorescer, and compounds which recognize a specific structure and bind to such structure are referred to as receptors and are normally antibodies.

The fluorescer which is chosen will have either a change in quantum yield or a change in its emission and/or absorption spectra or all of them, when the ligand analog-fluorescer is bound to receptor, as compared to being unbound. For the purposes of this assay, all that is required is that there be a change in the emission intensity at some wavelength or band of wavelengths.

In performing the assay, the method will vary depending upon whether the analyte is ligand or antiligand. The rate at which antiligand binds to ligand analog-fluorescer or the amount of antiligand bound to ligand analog-fluorescer at equilibrium will be related to the amount of available antiligand in the assay medium. Where the analyte is antiligand, the amount will be directly related to the amount in the sample, and when the analyte is ligand, the amount will be determined by the amount of ligand present in the assay medium in combination with a predetermined amount of antiligand. By observing the amount of reduction in the emission intensity with an unknown amount of analyte in comparison to an assay medium having a known amount of analyte, the amount of analyte in the unknown sample can be determined.

7 Claims, No Drawings

RECEPTOR FLUORESCENT IMMUNOASSAY

CROSS-REFERENCE TO RELATED APPLICATIONS

This application is a continuation-in-part of application Ser. No. 796,916, filed May 16, 1977, now abandoned which application is a continuation-in-part of application Ser. No. 751,838, filed Dec. 17, 1976, now abandoned which in turn is a continuation-in-part of application Ser. No. 402,693, filed Oct. 2, 1973, now U.S. Pat. No. 3,998,943.

BACKGROUND OF THE INVENTION

1. Field of the Invention

There is a continually expanding need to determine the presence of minute quantities of organic materials. Concentrations of interest range from about $10^{-4}$ to $10^{-12}$M or even lower. Areas where the determinations are significant include the presence of drugs of abuse in physiological media, the metering of therapeutic dosages of drugs, disease diagnosis, where the presence, absence or amount of a particular organic material is relevant to the diagnosis of the disease and assaying for trace components in food. Other areas which are not of physiological interest include scientific investigation and assaying for trace contaminants in water or other fluids, quality control, and the like.

One approach to assays for specific materials comes under the class of immunoassays. Immunoassays employ a receptor, normally an antibody, which recognizes a specific spatial structure and charge distribution—epitope—in an organic molecule. The antibodies are relatively large molecules, of 150,000 or greater molecular weight and are protein in nature. Therefore, with most organic compounds of interest, the binding of the antibody to the organic compound provides significant enhancement in molecular weight, as well as a change in the environment of the organic compound, as compared to the solvent environment. In immunoassays, aqueous solvents are normally employed.

In radioimmunoassay, the great enhancement in molecular weight allows for separation of an organic compound which is bound to antibody and unbound organic compound. By having a detector molecule which is radioactive, one can determine the distribution of the radioactive compound between bound and unbound. This distribution is related to the concentration of the organic compound present in the unknown.

A second technique is a spin immunoassay technique, supplied by Syva Company, under the trademark FRAT ®. In this technique, a stable free radical compound is bound to a compound resembling the unknown organic compound. The rate at which the spin label compound tumbles in solution affects the height of the electron spin resonance spectrum. When the spin label compound is bound to antibody, the rate is substantially slower than the unbound compound. By relating the peak height of the electron spin resonance spectrum to known standards, one can determine the amount of the unknown compound present in the solution.

Another technique uses an enzyme as the detector. In this technique, an enzyme is bound to the unknown compound and which is sold by Syva Company, under the trademark EMIT ®. When the enzyme-bound compound is bound to an antibody, there is a substantial reduction in the enzyme activity. Therefore, by metering the enzyme activity, and relating enzyme activity to a standard, one can determine the amount of unknown in a solution.

2. Description of the Prior Art

U.S. Pat. No. 3,709,868 is exemplary of a radioimmunoassay. U.S. Pat. No. 3,960,834 is exemplary of a spin immunoassay. U.S. Pat. No. 3,654,090 and German Auslegungsschrift No. 2,223,385 are exemplary of enzyme immunoassays. Articles of interest include an article by Ludwig Brand and James R. Gohlke, *Annual Review of Biochemistry*, 41, 843-868 (1972) and Stryer, *Science*, 162, 526 (1968). Smith, *FEBS Letters* 77, 25, (1977) describes a fluorescent immunoassay, where thyroxine is bound to a fluorescer and quenches the fluorescer, the quenching being reversed by binding of antibody to thyroxine. See also, Ullman et al, J. Bio. Chem. 251, 4172 (1976).

SUMMARY OF THE INVENTION

A fluorescent competitive protein binding immunoassay is provided for determining an analyte which is a member of an immunological pair-ligand and receptor for ligand (antiligand). The method involves conjugating a modified hapten ligand (ligand analog) to a fluorescer, by a relatively short chain, wherein the ligand analog is free of heavy atoms which catalyze the quenching of the fluorescer when in an excited electronic state. When antiligand is bound to the ligand analog-fluorescer, there is a reduction in emission intensity as compared to the ligand analog-fluorescer which is unbound. The amount of antiligand present in the assay medium will be related to the amount of antiligand present in an unknown sample or the amount of ligand present in the unknown sample in combination with a predetermined amount of antiligand. By comparing the emission intensity of the assay medium with an assay medium having a known amount of analyte, the amount of analyte in the unknown sample may be determined.

DESCRIPTION OF THE SPECIFIC EMBODIMENTS

A convenient simple sensitive assay is provided employing as a reagent a hapten free of heavy atoms capable of quenching fluorescence linked to a fluorescer, whereby binding of a receptor for the hapten reduces the emission intensity of the fluorescer upon irradiation of light in the absorption band of the fluorescer. In carrying out the subject assay, the analyte which is either ligand or receptor for the ligand (antiligand) is combined in an aqueous medium, normally buffered, with a reagent, which is a modified ligand, referred to as a ligand analog, linked to a fluorescing molecule by a relatively short chain. Where the analyte is ligand, a predetermined amount of antiligand will also be added. Binding of antiligand to the ligand analog-fluorescer results in a reduction in emission intensity of the ligand analog-fluorescer in the assay medium, when the assay medium is irradiated with light in the absorption spectrum of the fluorescer. By comparing the observed emission intensity of an assay medium containing an unknown amount of analyte with an assay medium having a known amount of analyte, the amount of analyte in the unknown may be determined.

DEFINITIONS

Ligand—any molecule for which a receptor is available or can be prepared and is free of heavy atoms, those atoms of atomic number 35 or greater, and has a molecular weight in the range of about 125 to 2,000, more usually in the range of about 125 to 1,000. The ligands will normally be haptenic.

Ligand analog—a group having substantially the same polar and spatial characteristics as the ligand and capable of competing with the ligand for antiligand, differing from the ligand in having a bond, hydrogen or functionality modified to provide for linking to a fluorophore.

Fluorescer—any molecule which fluoresces upon irradiation with light in the ultraviolet or visible region, and upon being electronically excited emits light at a longer wavelength. Preferably, the molecule has substantial absorption above about 350nm, more preferably above about 400nm.

Ligand analog-fluorescer—a molecule having the ligand analog linked to a fluorescer molecule by a bond or linking group, normally having a chain or from 1 to 20 atoms, more usually of from 1 to 12 atoms, and preferably of from about 2 to 8 atoms, which are carbon, oxygen and nitrogen, the linking group being composed solely of carbon, hydrogen, oxygen, sulfur and nitrogen, wherein the oxygen is present solely as oxy and oxo, particularly non-oxo carbonyl, nitrogen is present as amino, bonded solely to carbon, amido and imino, and sulfur being present as thiono or thio ether. Normally there will be from 1 to 6, more usually from 1 to 4 heteroatoms, particularly oxygen and nitrogen. The linking group may be aliphatic, alicyclic, aromatic, heterocyclic or combinations thereof, usually being aliphatic. There may be from 0 to 2, more usually 0 to 1 sites of ethylenic unsaturation, as the only aliphatic unsaturation. Particular functionalities involved are the non-oxo carbonyl (including the sulfur and nitrogen analogs thereof), oxy, carbamyl, thiourea, amido, amidino, urea, and thioamide.

Receptor—a macromolecule capable of binding to a specific spatial and polar organization (epitopic site), normally of at least about 15,000 molecular weight, and usually an antibody. Other receptors include Fab fragments, enzymes, and naturally Assay In performing the subject assay, the analyte and ligand analog-fluorescer are combined in an aqueous buffered medium, and when ligand is the analyte, a predetermined amount of antiligand is included in the assay medium. While the order of addition of the various materials is not critical, normally, the ligand analog-fluorescer will not be combined with antiligand, prior to the addition of the unknown sample, when ligand is the analyte. Normally, the rate of reversal of complex formation between an antibody and its correlative ligand is slow. If the ligand analog-fluorescer and antibody are combined prior to addition of ligand in the unknown, there would have to be a long incubation period until equilibrium was established. Preferably, either the ligand in the unknown sample and antiligand are combined, followed by the addition of ligand analog-fluorescer which then binds to the remaining available antiligand or the ligand in the unknown, ligand analog-fluorescer and antiligand are combined, so that the ligand and ligand analog-fluorescer can compete for the available binding sites of the antiligand. In some instances, where the unknown sample containing ligand and antiligand are combined initially, it may be desirable to incubate the mixture, normally for at least about one minute and usually not exceeding 24 hours, more usually being from about 5 minutes to 6 hours, and preferably being from about 5 minutes to 30 minutes.

The concentration of ligand which may be assayed will vary from about $10^{-4}$ to $10^{-15}$M, more usually from about $10^{-5}$ to $10^{-12}$M. The concentration of ligand analog-fluorescer will also vary in the same range, usually not differing by more than a factor of 100 from either the minimum or maximum concentration of interest. In an assay for ligand, the receptor concentration will generally be from about 0.5–1,000:1 in number of binding sites per mole of ligand analog-fluorescer, more usually 1–10:1 in number of binding sites per mole of ligand analog-fluorescer. See U.S. Pat. No. 3,690,834 for a method of determining binding sites. The mole ratio employed of receptor to ligand analog-fluorescer will depend to a significant degree on the binding constant of the receptor.

An aqueous medium is employed, generally having not more than about 20% by volume of a polar organic solvent. Various alcohols and ethers may be employed, generally of from 1 to 6 carbon atoms, more usually of from 1 to 4 carbon atoms.

The pH of the medium will normally be in the range of about 5 to 10, more usually in the range of about 7 to 9. Various buffers may be used to achieve the desired pH and maintain the pH during the determination. Illustrative buffers include borate, phosphate, carbonate, tris, barbital, and the like. The particular buffer employed is not critical to this invention, but in particular assays one buffer may be preferred over another.

With certain ligands and fluorescers, there may be a small but significant amount of non-specific binding of the ligand or fluorescer to protein. To that extent, it is preferred that the protein concentration of the assay medium be less than about 1 weight percent, preferably less than about 0.5 weight percent, and particularly preferred, less than about 0.1 weight percent. The total protein concentration may be minimized by prior treatment of the unknown sample by ultrafiltration, gel filtration, precipation, dialysis, and the like. Alternatively one can add sufficient excess protein to provide a constant amount of non-specific binding.

Moderate temperatures are normally employed for carrying out the assay and usually constant temperatures during the period of the assay will be employed. The temperatures normally range from about 0° to 50° C., more usually from about 15° to 40° C. and preferably from about 25° to 40° C. Higher temperatures are not desirable, since they reduce the binding of the antiligand to the epitopic sites.

In carrying out the determination, the assay solution is introduced into the fluorometer cell. The choice of excitation wavelength will depend on the fluorescer. The particular wavelength or band of wavelengths which are measured for the emission spectrum will depend on the emission maximum and the amount of interference due to light scattering. Desirably, an intense source of light of a single wavelength may be used. In this manner, interference from light scattering effects can be minimized. Useful monochromatic light sources that provide greater intensity than conventional sources coupled with a monochromator are low pressure emission lamps and lasers.

Assay Components

In performing the assay, the materials involved are the ligand, ligand analog-fluorescer, and receptor.

Ligand

As indicated previously, the ligand will normally be from about 125 to 2,000 molecular weight, more usually from about 125 to 1,000 molecular weight. The nature of the ligand may vary widely, subject only to the limitations that a receptor must be available or capable of being prepared; and the molecule is free of heavy atoms capable of quenching fluorescence, those atoms of greater than about 35 atomic number. These compounds involve a wide variety of compounds of varying structure, functionality, and physiological properties. The compounds may be acyclic, alicyclic or heterocyclic, both mono- and polycyclic. The heteroatoms involved include oxygen, nitrogen, sulfur, halogen (fluorine and chlorine) boron, phosphorous, metal cations of Groups 1A and 2A of the Periodic Chart and the like.

The functionalities include alcohols, ethers, carboxylic acids, esters and amides, amines (primary, secondary, tertiary and quaternary) halo, nitrilo, mercapto, and the like. Normally, the compounds will be composed solely of carbon, hydrogen, oxygen, nitrogen, halogen of not greater than atomic number 17, and phosphorous, particularly carbon, hydrogen, oxygen, and nitrogen, and where salts are involved, the appropriate metal counterion or ammonium counterion.

Heterocyclic rings which may be present include pyrrole, pyridine, piperidine, indole, thiazole, piperazine, pyran, coumarin, pyrimidine, purine, triazine, imidazole, and the like.

Because of the wide variety of compounds which can be determined in accordance with the subject assay, the different groups will be broken down into various, frequently artificial, categories, either by the presence of a particular functionality or ring structure, or because of sharing a particular function or because of being recognized as a class.

The first class of compounds of interest are those having an amino group, either as a heterocyclic member, or as a functionality on an aliphatic chain. These compounds will normally be of from about 110 to 800 molecular weight, more usually of about 125 to 650 molecular weight.

The first group of compounds of interest are the alkaloids and the metabolites of those alkaloids which are ingested. The first group of important alkaloids are alkaloids of the morphine group. Included in this group are morphine, codeine, heroin, morphine glucuronide and the like.

Compounds which find use in this invention as reagents for detecting morphine alkaloids and its metabolites will, for the most part, be of the following formula:

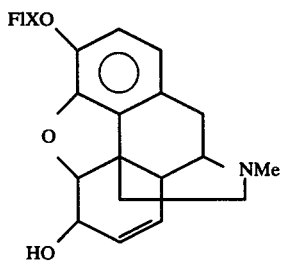

wherein X is a linking group, normally of from 2 to 8 atoms other than hydrogen, more usually of from 2 to 4 atoms other than hydrogen and being free of atoms other than carbon, hydrogen, oxygen, sulfur and nitrogen, and preferably having a non-oxo carbonyl group as part of the linking functionality. Fl is a fluorescer which will be described subsequently.

Illustrative linking groups are acetamido, acetimido, succinate, oxalate, and the like.

The next group of alkaloids are the cocaine alkaloids, which include, particularly as metabolites, benzoyl ecgonine and ecgonine.

Another group of alkaloids are the cinchona alkaloids which include quinine and quinidine.

The isoquinoline group of alkaloids includes mescaline.

The benzylisoquinoline alkaloids include papaverine.

The phthalide isoquinoline alkaloids include narcotine, narceine, and cotarnine.

The indolopyridocoline alkaloids include yohimbine and reserpine.

The ergot alkaloids include ergotamine and lysergic acid.

Other groups of alkaloids include styrchnine alkaloids, pyridine alkaloids, piperidine alkaloids, pyrrolizidine alkaloids, and the like.

The alkaloids of primary interest are those which come within the category of drugs of abuse, such as morphine, cocaine, mescaline, and lysergic acid, which may be analyzed for the compound or its metabolite, depending on the physiological fluid which is analyzed for its presence.

A number of synthetic drugs mimic the physiological properties, in part on in whole, of the naturally occurring drugs of abuse. Included among these drugs are methadone, meperidine, amphetamine, methamphetamine, glutethimide, diphenylhydantoin, and drugs which come within the category of benzdiazocycloheptanes, phenothiazines and barbiturates.

Drugs of interest because of their physiological properties are those which are referred to as catecholamines. Among the catecholamines are ephinephrine, ephedrine, L-dopa, and norephinephrine.

Another drug of interest is the tranquilizer Meprobamate.

Other compounds of interest are tetrahydrocannabinol, cannabinol, and derivatives thereof, primarily compounds derived from marijuana, synthetic modifications and metabolites thereof.

Another group of compounds of significant interest are the steroids. The steroids include estrogens, gestogens, androgens, adrenocortical hormones, bile acids, cardiotonic glycosides, aglycones, saponins and sapogenins.

Another class of compounds are the vitamins, such as vitamin A, the B group, e.g. vitamin $B_1$, E, K, and the like.

Another class of compounds are the sugars, both the mono- and polysaccharides, particularly di- and higher order polysaccharides.

Another class of compounds is the prostaglandins.

Another group of compounds are the antibiotics such as penicillin, actinomycin, chloromycetin, and the like.

Individual compounds of interest are serotonin, spermine, and phenylpyruvic acid.

Another class of compounds of interest are pesticides, such as fungicides, insecticides, bactericides, and nematocides.

Ligand Analog-Fluorescers

In most cases, the ligand analog will replace a hydrogen of the ligand with a bond to a linking group. As for example, with morphine, the hydrogen of the phenolic hydroxyl can be replaced with a bond to the methylene of a carboxymethylene group. The hydrogen which is replaced by a bond to a linking group may be bonded to carbon, either aliphatic or aromatic, oxygen or nitrogen.

In some instances, an oxocarbonyl may serve as the linking site by modifying the oxocarbonyl to an oxime. In other instances, the hydroxyl of a carboxyl group may be replaced to form a linking group, by forming an ester or amide.

Additional alternatives include introducing functionalities, such as hydroxyl functionalities from which ethers can be formed, amino functionalities, from which diazo groups can be formed, and the like.

The significant factor for the ligand analog is that it has sufficient structural similarity to the ligand so as to be recognized by the antibody for the ligand. Because the manner of addition can be widely varied, the binding constants for the ligand and the ligand analog may be different, but should not differ by more than a factor of $10^3$, preferably by not more than a factor of $10^2$.

For the most part, the ligand analog will have the same or substantially the same structure and charge distribution (spatial and polar organization) as the ligand for a significant, if not major, portion of the molecular volume. Since frequently the linking site for a hapten will be the same in preparing the antigen for production of antibodies as used for linking to the fluorescer, the same portion of the ligand molecule which provides the template for the antibody will be exposed by the ligand analog when bound to fluorescer.

Usually, the linking group will be less than about 25Å, more usually less than 20Å, and preferably less than about 15Å in length in solution. Desirably, the linking group in solution will be in the range of about 1.5 to 10Å. It is postulated that the reduction in emission intensity when ligand analog is bound to receptor results from at least a portion of the fluorescer molecule being also in the binding site of the receptor. It is found that the nature of binding sites with antibodies does vary with successive bleeds, and the size of the binding site cleft may increase with increasing affinity. See Macario and Macario, Immunochemistry 12 249 (1975). Therefore, it may be envisioned that as the ligand goes deeper into the cleft of the antibody, the adjacent fluorescer is also drawn into the cleft and affected by the surrounding protein.

In choosing the fluorescer, a wide variety of considerations will come into play. As already indicated, the choice of fluorescer will, to a degree, be governed by the ligand. Therefore, one consideration is that the fluorescer have absorption at higher wavelengths than a fluorescent ligand or ligand bound to antibody.

In addition to the considerations which relate to the particular ligand being determined, there will be a number of other considerations which limit the particular choice of fluorescer. As a practical matter, since one is concerned with a change in the emission spectrum as a result of being bound or unbound to an antiligand, one would desire a large environmental effect on the emission intensity at a particular wavelength. This can be a result of a substantial change in quantum yield or a change in the emission or absorption spectrum in going from the bound to unbound ligand analog-fluorescer.

Since proteins absorb at a wavelength of about 280, the fluorescer should have an absorption maximum above 300, usually above 350 and preferably above 400. The extinction coefficient should be greatly in excess of 10, preferably in excess of $10^3$, and particularly preferred, in excess of $10^4$.

In addition, it is desirable that the fluorescer have a large Stokes shift. That is, it is preferred that there be a substantial spread or difference in wavelengths for the fluorescer between its absorption maximum and emission maximum.

Another consideration where physiological fluids are concerned is non-specific binding of the fluorescer to protein. Preferred fluorescers will have minimal non-specific binding or a minimal change in their fluorescence upon non-specific binding, so that the primary or sole effect seen is the binding of the fluorescer to its antibody.

A number of different fluorescers are described in the articles previously noted; namely, Stryer, supra and Brand, et al, supra.

One group of fluorescers having a number of the desirable properties described previously are the xanthene dyes, which include the fluoresceins derived from 3,6-dihydroxy-9-phenylxanthhydrol and rosamines and rhodamines, derived from 3,6-diamino-9-phenylxanthhydrol. The rhodamines and fluoresceins have a 9-o-carboxyphenyl group, and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-napththa-lene sulfonate and 2-p-toluidinyl-6-naphthalene sulfonate. Some naphthalene compounds are found to have some non-specific binding to protein, so that their use requires employing in an assay media where the amount of protein is minimized.

As already indicated, the linking group may be derived from a functionality which is present on the fluorescer or a functionality which is present on the ligand analog. The fluorescer and/or ligand analog may be modified in order to provide the necessary linkage between the two compounds.

The following examples are by way of illustration and not by way of limitation.

EXPERIMENTAL (All temperatures not otherwise indicated are in centigrade.)

I. Preparation of dansyl-BSA (bovine serum albumin) conjugate

Into a scintillation vial was placed 10.0 mls of 0.1M $PO_4$ buffer, pH 7.0 and 500mg BSA ($7.8 \times 10^{-6}$M) (Miles Labs.). Then, 100mg 1-dimethylaminonaphthyl-5-sulfuryl chloride (DANSC) ($3.7 \times 10^{-4}$ Moles) (Seikagaku Kogyo Ko. Ltd., Japan) was added in 1ml acetone, and the mixture was stoppered, covered with aluminum foil, and placed in the center hole of a vortex mixer and shaken at low speed overnight. The following morning, excess DANSC was removed by filtration through a plug of cotton. The filtrate was applied to a 5×70cm column of Sephadex G-25 and eluted with 0.1M PO$_4$, pH 7.0, flow rate 50 mls/hr, collecting 9ml fractions. Fractions 57-76 were pooled (yellow-orange in color) and concentrated by ultrafiltration through Dow hollow fibers. The concentrated solution had a protein content of 4 mgs/ml. This solution was adjusted to 0.15M NaCl and filtered through 0.25μ Millipore filters to sterilize. Samples of 2ml volume were put into sterile vials for making up injections.

Ultraviolet analysis of the dansyl-BSA conjugate confirm the presence of dansyl on BSA by its absorption at 340 mμ. By utilizing the experimentally determined value of ε for dansyl on protein of $3.3 \times 10^3$ the hapten number for this conjugate is 13.5 dansyl/BSA.

The fluorescence properties of this conjugate were examined briefly. The parameters were: excitation maximum at 338 mμ, emission maximum at 498 mμ.

II. Preparation of insulin-dansyl conjugate

Into a scintillation vial containing 3 ml of saturated NaHCO$_3$ was placed 16.7 mg ($2.9 \times 10^{-6}$ Moles) of porcine insulin. To this solution was added 9.6 mg ($3.6 \times 10^{-5}$ Moles) of DANSC dissolved in 1 ml of dioxane. A yellow precipitate appeared immediately which dissolved upon addition of 0.5 ml dioxane. To clear up a very faint white precipitate (carbonate) 0.5 ml H$_2$O was added. This solution was then capped and covered with aluminum foil, placed in the center hole of a vortex mixer and shaken gently overnight. The next morning the solution was acidified to pH 5 with acetic acid, then applied to a 2.5×30 cm column of Sephadex G-10 and eluted with 0.2 M HOAc, flow rate 10 ml/hr. Fraction volume was 1.6 ml. Four peaks were observed. The first peak (Fractions 17-22) exhibited fluorscence emission and excitation spectra typical of dansyl-protein conjugates.

III. Preparation of fluorescein-BSA conjugate

Into a scintillation vial was placed 180 mgs of BSA ($2.6 \times 10^{-6}$ Moles) (Pentex, crystallized) dissolved in 6 mls H$_2$O containing 180 mgs K$_2$CO$_3$. To this was added 18.3 mgs fluorescein isothiocyanate (FITC) ($4.85 \times 10^{-5}$ Moles) and the mixture was stoppered, covered with aluminum foil then placed in the center hole of a vortex mixer and shaken gently overnight at room temperature. The following morning the reaction mixture was acidified to pH 4 with 1N HCl (heavy precipitate), then made basic to pH 8 with 0.1N NaOH, applied to a 2.5×30 cm column of Sephadex G-10 and eluted with 0.05M PO$_4$, pH 8.0 at 5.4 mls/hr, 0.9 ml/fraction. Fractions 43-72 were pooled. Hapten number was calculated from the UV absorption of the conjugate at 493 mμ and the extinction coefficient for protein-bound fluorescein of $7.2 \times 10^4$. Hapten number was thus calculated to be 14.5.

IV. Preparation of insulin-fluorescein conjugate

Into a scintillation vial was placed 35.1 mgs porcine insulin ($6.1 \times 10^{-6}$ Moles) dissolved in 3.5 mls of 0.1M CO$_3$ buffer, pH 9.2, 0.15M NaCl. To this solution was added 4.8 mg FITC ($1.2 \times 10^{-5}$ Moles) and the vial stoppered, covered with aluminum foil and placed in the center hole of a vortex mixer for gentle shaking overnight. The following morning the mixture was acidified to pH 3 with 1N HCl (bubbling) resulting in precipitation of fluorescein thiocarbamyl insulin then made basic once more with 1N NaOH just until all the precipitate was in solution. This orange solution was applied to a 2.5×35 cm column of Sephadex G-10 and eluted with 0.05M PO$_4$, pH 7.4, 0.15M NaCl. Elution rate was 12 ml/hr, 2 ml fractions. Fractions 24-33 were highly fluorescent and were pooled. These fractions were applied directly to a 2.5×30 cm column of DEAE Sephadex A-25 which had been pre-equilibrated with 0.05M Tris, pH 7.1, 7M urea, 0.1M NaCl. After application, elution was 12 mls/hr, 2 mls/fraction, with a linear sodium chloride gradient from 0.1M to 1.0M over 500 mls. Salt concentration was maintained at 1.0M until the final (4th) peak was completely eluted, with monitoring at 280 mμ. The first peak was column washings, the second, unreacted insulin, then mono-, di-, tri-fluorescein insulin in that order. Purity was assessed by electrophoresis on CAM, Tris-barbital buffer, pH 8.8. Current was continued for 50 minutes, 125 v, and staining was with Ponceau S. All spots were fluorescent.

V. Preparation of morphine-fluorescein conjugate

Into a reaction vessel was introduced 68.8 mg (0.2 mmol) O$^3$-carboxymethylmorphine in 2 ml DMF, the mixture cooled to −5° C. and 26 μl (0.2 mmol) isobutyl chloroformate added. The mixture was then stirred for 45 minutes. The resulting solution was then added slowly in 0.05 ml portions to 36 mg 4-aminofluorescein hydrochloride (Sigma isomer II.HCl) in 1 ml butanol cooled in an ice bath. The mixture was allowed to stand 90 min. before workup.

The reaction mixture was streaked directly on a preparative thin layer chromatograph and eluted with CHCl$_3$; MeOH; HOAc (75:50:10). After repeating the chromatography, the product was extracted from the silicon gel with methanolic sodium hydroxide. The methanol was evaporated, water added, and the resulting precipitate was rinsed thoroughly. The product was redissolved in methanolic sodium hydroxide, water added, the methanol evaporated and the pH adjusted to 8.0 with HCl to provide a solution of the desired product.

VI. Preparation of thyroxine-fluorescein conjugate

Into a reaction flash was introduced 165 mg. (0.2 mmole) of methyl throxinate hydrochloride, 8 ml freshly distilled tetrahydrofuran and 15 ml aqueous carbonate buffer (pH 9.2, 0.1M). After degassing with nitrogen, 77.8 mg (0.2 mmole) of FITC in 2 ml 1:1 THF/carbonate buffer was added over a period of 5 minutes with agitation. The pH which had dropped to 7.8 was adjusted to 9 with 2N NaOH.

After storing in a freezer overnight, the mixture was poured into 20 ml ethyl acetate/20 ml 1N HCl, the layers separated, the aqueous layer washed one time with 20 ml ethyl acetate and the organic layers combined. The organic layers were washed 4×30 ml 1N HCl and 2×200 ml brine, dried over magnesium sulfate and the volatiles removed in vacuo.

To further purify the product, a preparative TLC was employed using 100 mg silica gel and developed with a solvent 95 vol % (25 vol % diethyl ether/75 vol % CH$_2$CL$_2$)/5 vol % glacial acetic acid. The middle bond was separated, extracted with THF and the solvent evaporated to leave 75 mg. The residue was rechromatographed employing the same solvent system and silica gel to yield 55 mg of the desired product.

VII. Preparation of diphenylhydantoin conjugate to fluorescein

To a stirring solution of 1-carboxymethyldiphenylhydantoin in dry DMF under $N_2$ was added drop wise one mole equivalent of $SOCl_2$. After stirring the solution overnight at room temperature, the solvent was removed in vacuo and one equivalent each of triethylamine and fluorescein amine added in dry DMF and the mixture stirred for 24 hours. The solvent was partially removed in vacuo and the residue purified with preparative tlc (silica gel; methanol-chloroform 1:1 (vol)). The fast moving fluorescent band was shown to have diphenylhydantoin and be the desired product.

VIII. Conjugations with N-glycyl fluorescein amine

A. In 50 ml of ethyl acetate was suspended 1.04 g of fluorescein amine, one equivalent of chloroacetyl chloride added and the mixture refluxed under anhydrous conditions for four hours. The product precipitated out as a yellow solid and was purified by preparative tlc (silica gel ($HCCl_3$—MeOH; 3:1 (vol)). A solution of 50 mg of N-chloroacetyl fluorescein amine in 20 ml ethanol (anh) was saturated with ammonia, the vessel sealed and the reaction mixture stirred for 48 hours at room temperature. Upon removal of solvent the desired product as a yellow solid was obtained.

B. To a stirring solution of the desired carboxylic acid (1) and triethylamine (2) in 0.5 ml dry DMF at $-10°$ was added isobutylchloroformate (3). After 0.5 hrs, an excess of N-glycyl fluoresceinamine in dry DMF was added, the mixture stirred overnight, followed by solvent removal in vacuo. The product was purified by preparative tlc (silica gel: $HCCl_3$—MeOH 1:1 (vol)) and the fast moving band shown to have the compound of interest as a fluorescing compound.

| (1) | (2) | (3) |
|---|---|---|
| 5-phenyl-5-(4'-crotonic acid)-barbituric acid, 5 mg | 1.7 mg | 2.3 mg |
| N-(5'-carboxy-n-phentylcarbonyl)dibenzazepine, 5 mg | 1.4 mg | 1.9 mg |
| 0-carboxylmethyloxime of 3-ketodigoxigenins, 5 mg | 1.1 mg | 1.5 mg |

IX. Conjugation of rhodamine to anti(fluorescein)

A 1 ml aliquot of antisera to fluorescein was precipitated against 50% saturated ammonium sulfate, and the precipitate dissolved in 1 ml of 0.1M $K_2HPO_4$ and dialyzed against the same solution to yield a solution having a concentration of 9 mg/ml. Into a reaction vessel was introduced 0.4 ml (3.6 mg) of the anti(fluorescein) antisera and 0.17 ml of glycerol, the pH brought to 9.5 and 0.8 mg of tetramethylrhodamine isothiocyanate in 100 μl DMF added with stirring at room temperature. After continuing the reaction for 3 hrs., the solution was poured onto a Sephadex LH-20 column (0.9×15 cm) and the anti(flourescein) recovered in 1 ml.

In order to establish the utility of the subject compounds, the following assays were carried out. It was found that various instrument cells gave different results, so that absolute values could only be compared where the same cell was employed. The fluorometer employed was a Perkin-Elmer MPF-2a. Antibodies to the fluorescers had been prepared according to normal procedures. The bovine serum albumin conjugates were injected into sheep, and after appropriate periods of time, the antibodies harvested according to conventional techniques. For typical methods of obtaining antibodies, see Microbiology, Hober Medical Division, Harper and Rowe, 1969; Landsteiner, Specificity of Seriological Reactions, Dover Publications, New York, 1962; Kabat, et al, supra; and Williams, et al, Methods in Immunology and Immunochemistry, Vol. 1, Academic Press, New York, 1967.

The reagents which were employed were as follows: FLUMO (fluorescein-morphine conjugate, Example V) was $3\times10^{-6}$M in water; antifluorescein was $5.6\times10^{-6}$M in binding sites, in water, 0.05M phosphate, pH 8.0; anti-morphine was $2\times10^{-4}$M in binding sites, 0.05M tris-HCl, pH 8.0, in saline solution; buffer was Tris/saline 0.05M/l, pH 8,0. Opiate solutions had 1,000 μg/ml of codeine. The solution was then diluted to a final volume of 4 ml with buffer.

All of the determinations were made at a sensitivity setting on the instrument of 4. The solutions were mixed in order from left to right as set forth in the table. Excitation light was 460 nm and the emitted light read at 516 nm, with a band width of 10 nm.

The following table indicates the results.

TABLE I

| Cell No | Fluorescein-Morphine Vol. μl | Anti-Fluorescein Vol. μl | Anti-Morphine Vol. μl | Codeine Vol. μl | Signal Intensity | Reading Time min. |
|---|---|---|---|---|---|---|
| 2 | 5 | — | — | — | 62 | — |
| 2 | 5 | 5 | — | — | 21 | |
| 2 | 5 | 5 | 5 | — | 25 | |
|   |   |   |   |   | 26.5 | 5 |
|   |   |   |   |   | 27.5 | 90 |
| 4 | — | — | — | — | 8 | |
| 4 | — | 5 | — | — | 3.5 | |
| 4 | — | 5 | 5 | — | 3.5 | |
|   |   |   |   |   | 5 | 5 |
|   |   |   |   |   | 5.5 | 90 |
| 3 | — | — | — | — | 1.5 | |
| 3 | 5 | — | — | — | 46 | |
| 3 | 5 | — | 5 | — | 35.5 | |
|   |   |   |   |   | 35 | 5 |
| 3 | 5 | 5 | 5 | — | 23 | |
|   |   |   |   |   | 22.5 | 5 |
| 3 | 5 | 5 | 5 | 5 | 20 | |
|   |   |   |   |   | 16 | 90 |
| 1 | — | — | — | — | 11 | |
| 1 | — | 5 | — | — | 14.5 | |
| 1 |   |   |   |   | 14.5 | 5 |

TABLE I-continued

| Cell No | Fluorescein-Morphine Vol. μl | Anti-Fluorescein Vol. μl | Anti-Morphine Vol. μl | Codeine Vol. μl | Signal Intensity | Reading Time min. |
| --- | --- | --- | --- | --- | --- | --- |
| 1 | — | 5 | 5 | — | 5 |  |
| 1 | — | 5 | 5 | 5 | 5.5 |  |
|  |  |  |  |  | 6 | 90 |

Where a reading is given but the absence of any material is indicated, only buffer was present in the cell. The reading times indicate the interval of time from the time of the first reading to the reading for the result which is reported, the first reading being made within as short an interval as possible of the mixing.

The results show that in the absence of any competition between codeine and fluorescein-morphine, the readings are relatively stable. Cell No. 2 changes 2.5 units in signal intensity over a period of 90 minutes, 1.5 units of the change having occurred in the first 5 minutes. The results in cell No. 4 demonstrate that with only the antibodies, the major change in the reading occurs in the first 5 minutes, a change of only 0.5 units occurring over a period of 85 minutes. The results in cell No. 1 show substantial stability in the readings where codeine is added to a mixture of the two antibodies. There is only a change of 0.5 units over a period of 90 minutes. Finally, the results in cell No. 3 show that with both antibodies in the presence of codeine and fluorescein-morphine, a change of 6.5 units in signal intensity is achieved over a period of 90 minutes.

Therefore, a detectable change in fluorescence is obtained when codeine is introduced into a mixture of the fluorescein-morphine and antibodies to both fluorescein and morphine.

In cell No. 3, when fluorescein-morphine is combined with antimorphine, there is an approximately 25% reduction in signal intensity. Therefore, the amount of antimorphine present in an assay medium could be determined by the reduction in signal intensity observed when an unknown sample suspected of containing antimorphine is combined with morphine-fluorescein. The method also provides a practical assay for morphine, since by combining a predetermined amount of antimorphine with morphine and then adding the mixture to the morphine-fluorescein, the amount of available antimorphine for binding to the morphine-fluorescein will be controlled by the amount of morphine present in the unknown sample.

To demonstrate an assay for codeine, the following assay was carried out. Dilution of antisera and of the fluorescein-morphine conjugate of Example V were made with aqueous 0.05M phosphate, pH 8. Different antisera were employed and the amount of quenching by the antisera determined. Employing one of the antisera, the morphine-fluorescein conjugate was then combined, followed by the addition of codeine to varying concentrations. The following tables indicate the results.

TABLE 1

| Antimorphine | | Quenching |
| --- | --- | --- |
| $Ka^1$ | $Ab, M^1$ | % |
| $9.1 \times 10^7$ | $1.6 \times 10^{-8}$ | 23 |
| $2.3 \times 10^6$ | $1.0 \times 10^{-7}$ | 31 |
| $5.2 \times 10^6$ | $3.9 \times 10^{-8}$ | 27 |
|  | $7.8 \times 10^{-8}$ | 30 |

[1]Binding constant and binding site concentration based on a free radical method of determination. See U.S. Patent No. 3,853,914

TABLE 2

| Operation | | Concentration, M | | | Fluorescence Signal (arbitrary units) |
| --- | --- | --- | --- | --- | --- |
|  |  | Ex. V | Anti-Morphine | Codeine |  |
| 3.5ml | $1.9 \times 10^{-8}$ M Ex. V | $1.9 \times 10^{-8}$ | — |  | 79 |
| +3μl | $2 \times 10^{-5}$ M anti-M | " | $1.7 \times 10^{-8}$ | — | 58.5 |
| +2μl | $1.67 \times 10^{-4}$ codeine | " | " | $9.5 \times 10^{-8}$ | 61 |
| +2μl | $1.67 \times 10^{-4}$ codeine | " | " | $1.9 \times 10^{-7}$ | 62.5 |
| +10μl | $1.67 \times 10^{-4}$ codeine | " | " | $6.7 \times 10^{-7}$ | 64.5 |

It is evident from the above results that about 30% of the fluoroescence quenched by the anti-morphine is recovered with the addition of codeine. A concentration of codeine of about $10^{-7}$ is detectible with the particular materials employed.

In the next study, a diphenylhydantoin-fluorescer conjugate was combined with a number of different antisera obtained with different conjugates of diphenylhydantoin to antigens. The amount of quenching was determined for each of the antisera. In addition, a number of determinations were made with varying concentrations of diphenylhydantoin, demonstrating an assay for diphenylhydantoin.

The following procedure was employed. The drug solution (25 μl) was diluted with 250 μl of 0.1M borate buffer, pH 8.0, and introduced into a test tube. To the solution was then added 25 μl of buffer for antibody, followed by 25 μl of the diphenylhydantoin-fluorescein conjugate to provide $1.04 \times 10^{-8}$M in the assay medium and 250 μl of buffer. After mixing vigorously, the mixture was incubated, 2ml of buffer added, the mixture mixed again and aspirated into a fluorometer. The readng is taken after a 15 sec. delay. The conjugate in the absence of antibody was set at 1,000 with a 50× gain, with the buffer zeroed at 50× gain. The following table indicates the results.

TABLE 3

| Antisera[1] Vol μl | Conjugate[2] vol. μl | DPH[3] vol. μl | Fluorescent Signal arbitrary units |
| --- | --- | --- | --- |
| 1 25 | 0 | 0 | 4 |
| " | 25 | 0 | 524 |
| " | 25 | 0 | 562 |
| " | 25 | 25 | 745 |
| " | 25 | 25 | 736 |
| 2 " | 0 | 0 | 26 |
| " | 25 | 0 | 752 |
| " | 25 | 0 | 774 |

TABLE 3-continued

| Antisera[1] | Vol μl | Conjugate[2] vol. μl | DPH[3] vol. μl | Fluorescent Signal arbitrary units |
|---|---|---|---|---|
| | " | 25 | 25 | 1025 |
| | " | 25 | 25 | 1028 |
| 3 | " | 0 | 0 | 21 |
| | " | 25 | 0 | 733 |
| | " | 25 | 0 | 779 |
| | " | 25 | 25 | 1031 |
| 4 | " | 0 | 0 | 40 |
| | " | 25 | 0 | 757 |
| | " | 25 | 0 | 728 |
| | " | 25 | 25 | 922 |
| | " | 25 | 25 | 900 |
| 1 | 2 | " | 0 | 838 |
| | 2 | " | " | 839 |
| | 5 | " | " | 633 |
| | 5 | " | " | 731 |
| | 10 | " | " | 575 |
| | 10 | " | " | 603 |
| | 5 | " | " | 668 |
| | 5 | " | " | 645 |
| | 1 | " | " | 926 |
| | 1 | " | " | 862 |

[1]The antisera were obtained from bovine serum albumin conjugates with the following diphenylhydantion analogs:

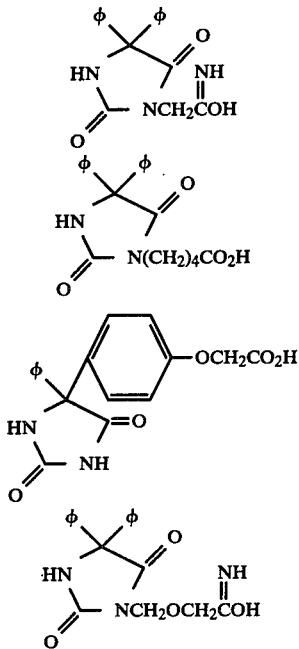

1.
2.
3.
4.

See U.S. Patent Application No. 484,026, filed June 28, 1974, now abandoned for the preparation of the compounds.
[2]After ammonium sulfate precipitation of serum, the precipitate was reconstituted to approximately the original serum volume with buffer and then diluted 1:10 with 0.1M borate buffer, pH 8.
[3]Concentrations: 3mg/ml The above procedure was repeated, except that drug solutions of varying concentrations were employed. Antisera 1 was employed adding 5 μl and 25 μl of the diphenylhydantion-fluorescein conjugate. The following table indicates the results.

TABLE 4

| DPH conc. mg/ml | Fluorescent Signal (arbitrary units) |
|---|---|
| 3 | 904 |
| 3 | 885 |
| 0.3 | 788 |
| 0.3 | 792 |

TABLE 4-continued

| DPH conc. mg/ml | Fluorescent Signal (arbitrary units) |
|---|---|
| 0.03 | 725 |
| 0.03 | 728 |

The above data demonstrate that a successful assay can be carried out for a wide variety of compounds, both ligands and receptors. In addition, it is found that the amount of quenching observed is related to the particular antisera. This may be affected by the animal source, the structure of the antigenic conjugate for haptens, and the particular bleed.

In accordance with the subject invention, a simple rapid assay is provided which employs stable reagents and has a simple protocol. Both ligands and receptors may be determined. The assay is predicated upon the ability to observe quenching of fluorescence, when a fluorescer is conjugated to a ligand and antiligand is bound to the ligand portion of the conjugate. In the presence of ligand, the amount of antiligand available for binding to the conjugate is diminished, so that enhanced fluorescence is observed.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of a ligand in a sample, when the ligand is of a molecular weight in the range of about 125 to 2,000 and free of heavy atoms of atomic number greater than 35, said method comprising:
   combining in an aqueous medium
   said sample;
   ligand analog-fluorescer wherein said ligand analog has at least one common epitope with said ligand so as to be specifically recognizable by a common antibody, and the ligand analog and fluorescer are linked sufficiently close by a linking group, so that the binding of antiligand to ligand analog reduces the emission intensity of said fluorescer having an aborption maximum above 300 mμ;
   antiligand;
   determining at at least one wavelength the intensity of the emission from said medium as compared to a standard having a known amount of ligand, by irradiating said medium with light in the absorption band of said fluorescer.

2. A method according to claim 1, wherein said aqueous medium is at a pH in the range of about 5 to 10 and at a temperature in the range of about 15° to 40° C.

3. A method according to claim 2, wherein the concentration of ligand analog-fluorescer is in the range of about $10^{-4}$ to $10^{-12}$M.

4. A method according to claim 2, wherein said ligand has a molecular weight in the range of about 125 to 1,000.

5. A method according to claim 4, wherein said ligand is morphine.

6. A method for detecting the presence of a ligand in a sample, wherein said ligand has a molecular weight in the range of about 125 to 2,000, said method comprising:
   combining in an aqueous medium at a pH of about 6 to 9 said sample;
antiligand; and
ligand analog-fluorescer at a concentration in the range of about $10^{-4}$ to $10^{-12}$M, wherein said ligand analog has at least one common epitope with said ligand, so as to be specifically recognizable by a common antibody, and the ligand analog and fluorescer are linked together at an average distance of less than about 25Å, so that binding of antiligand to ligand analog results in reduction of the emission intensty of said fluorescer, wherein said fluorescer has an absorption maximum above 350 m$\mu$; and determining at at least one wavelength the intensity of the emission from said medium as compared to a standard having a known amount of ligand, by irradiating said medium with light within the absorption band of said fluorescer.

7. A method according to claim 6, wherein said fluorescer is selected from the group consisting of fluoresceins, rosamines, and rhodamines.

* * * * *